United States Patent
Tsujii

Patent Number: 5,915,242
Date of Patent: Jun. 22, 1999

[54] WORKSTATION FOR MEDICAL SERVICE

[75] Inventor: Osamu Tsujii, Yokohama, Japan

[73] Assignee: Canon Kabushiki Kaisha, Tokyo, Japan

[21] Appl. No.: 08/870,380

[22] Filed: Jun. 6, 1997

Related U.S. Application Data

[62] Division of application No. 08/180,065, Jan. 11, 1994, Pat. No. 5,675,744.

[51] Int. Cl.$^6$ ....................................................... G06F 3/00
[52] U.S. Cl. ............................................... 705/3; 235/375
[58] Field of Search ............................. 283/76; 358/434; 250/208.1; 235/375; 705/3

[56] References Cited

U.S. PATENT DOCUMENTS

| | | | |
|---|---|---|---|
| 4,491,725 | 1/1985 | Pritchard | 235/375 |
| 4,619,469 | 10/1986 | Grover | 283/76 |
| 4,632,428 | 12/1986 | Brown | 283/76 |
| 4,847,694 | 7/1989 | Nishihara | 358/434 |
| 4,858,121 | 8/1989 | Barber et al. | 364/406 |
| 4,958,283 | 9/1990 | Tawara et al. | 364/413.13 |
| 5,270,530 | 12/1993 | Godlewski et al. | 250/208.1 |
| 5,291,399 | 3/1994 | Chaco | 364/413.02 |

OTHER PUBLICATIONS

HP–UX Reference, vol. 3: Sections 1M, 4, 5 and 7, pp. 790–798, Aug., 1992.
Catalogue of RSTAR, Inc., 1992.
PCS, The Advanced Nuclear Medicine Computer (Picker International), 1986.
SPIE vol. 1654 Medical Imaging VI: PACS Design and Evaluation (1992); pp. 306–319 relates to a public circuit.
SPIE vol. 1654 Medical Imaging VI: PACS Design and Evaluation (1992); pp. 455–466 relates to an exclusive circuit.

Primary Examiner—Kevin J. Teska
Assistant Examiner—Russell W. Frejd
Attorney, Agent, or Firm—Fitzpatrick, Cella, Harper & Scinto

[57] ABSTRACT

A system bus for connecting modules in a workstation for medical service has connected thereto a CPU, a main memory device, an input-output apparatus comprising a CRT or a display device such as liquid crystal and an operation input device, an ISDN interface, a disc and an optical card device. A list of data structural bodies stored in an optical card carried by a patient is read by the optical card device, and data access is effected to facilities which seem to require data reference by the use of a facility line number recorded on the optical card, through the ISDN interface.

1 Claim, 4 Drawing Sheets

FIG.3

| FACILITY IDENTIFICATION CODE |
| --- |
| FACILITY LINE NUMBER |
| PERSONAL IDENTIFICATION CODE |
| PERSONAL PASSWORD |
| CONSULTATION SECTION CODE |
| LATEST CONSULTATION DATE |

WORKSTATION FOR MEDICAL SERVICE

This application is a division of application Ser. No. 08/180,065, filed Jan. 11, 1994, now U.S. Pat. No. 5,675,744.

BACKGROUND OF THE INVENTION

1. Field of the Invention

This invention relates to workstations for medical service which are mutually connected through public or exclusive digital circuits and enable the utilization of medical service information by those workstations, in common.

2. Related Background Art

Workstations for medical service have heretofore been called PACS (Picture Archiving and Communication System) and produced as commodities, and are generally comprised of a general purpose computer, a high accuracy CRT, an image input apparatus, a local area network interface and a medical service information file. Teleradiography terminals utilizing analog or digital public circuits are produced as regional connections.

SUMMARY OF THE INVENTION

In recent years, the current of the unification of the standards of the data formats of medical service information is rapid and is on the trend toward not managing data by formats unique to manufacturers or unique to products, but managing data by standards such as the United States' ACR/NEMA (the American College of Radiology/the National Electrical Manufacturers Association) and Japan's MIPS (Medical Image Processing System, which is modified from the standard of the ACR/NEMA in Japan). If such unification of standards progresses, utilization of data among different manufacturers as well as among different facilities (hospitals) will become possible. In the present situation, however, no effective method has been proposed for the timing and procedures needed to permit common utilization of the same data by plural facilities.

It is the object of the present invention to provide a workstation for medical service which achieves the decentralized management and reuse of medical service information between facilities with good timing and effectively.

To achieve the above object, a first workstation for medical service according to the present invention has public or exclusive digital circuit interface means, and means for reading and writing data in a removable memory medium having stored therein one or more data structural bodies having at least one of a facility identification code, a facility line number, a personal identification code and a personal password, and is characterized in that the data retrieval of medical service information in other facilities is line by the use of the facility line number.

A second workstation for medical service has public or exclusive digital circuit interface means, and means for reading data from a removable memory medium having stored therein a datum having at least one of an insurance organ code, an insurance organ line number, an insurant identification code and an insurant password, and is characterized in that the insurance organ line number, the insurant identification code and the insurant password are used to read out the facility identification code and the facility line number utilized by the insurant and the whole or a part of the data structural body comprising the personal identification code and the personal password, and the one or more data structural bodies are used to access to the medical service information in other facilities.

The workstation for medical service of the above-described construction according to the present invention has public or exclusive digital circuit interface means, and means for reading and writing data in a removable memory medium, and uses the facility line number stored in the removable memory medium to effect the data retrieval of the medical service information in other facilities.

BRIEF DESCRIPTION OF THE DRAWINGS

FIG. 3 is an illustration of the data structural body of an optical card.

DETAILED DESCRIPTION OF THE PREFERRED EMBODIMENT

A workstation for medical service according to the present invention utilizes a removable memory medium (hereinafter referred to as the card) owned by each patient for the utilization in common of personal medical service information among facilities. In the card, there are written a facility identification code, a facility line number, a personal identification code and a personal password for each hospital utilized by the patient. This information is written when the patient visits each hospital for the first time.

The facility identification code is a code for specifying a hospital in the utilization area for the workstation for medical service, and in Japan, the code corresponds a code used in a hospital when any insurance is applied to a patient and the like. The facility line number is the number of a digital circuit, and in the case of Japan, it is a circuit number issued by NTT (Nippon Telegraph And Telegram Public Cooperation). For small-to-medium sized hospitals, an ISDN (Integrated Services Digital Network) which can also function as a telephone system, is more efficient. The personal identification code is one used to identify the particular patient, and need not be the same for a given patient in all hospitals. The personal password is a password set for each patient in each hospital, and may be used as a set with the personal identification code, whereby it may be utilized to maintain secret, information relating to the patient's medical history.

In the workstation for medical service according to the present invention, public circuits are often utilized and in the case of a public circuit, the personal password is used as protection when a third person enters the circuit with a suitable personal identification code to thereby reduce the probability that the third person enters the circuit. It is conceivable to make the personal identification code extremely long to thereby reduce the probability of intrusion by the personal identification code alone, but in a medical image or the like, it is a usual practice to imprint the personal identification code into a corner of data, so a very long personal identification code would present a problem in itself.

The above-described four data are the minimum necessary data in the workstation for medical service. Besides these four data, it is also conceivable to identify the section consulted, such as the internal medicine department, the department of ophthalmology or gynecology, etc., and the latest consultation date, in the card. These data written in each hospital are referred to as a data structural body. If a certain patient has visited for example ten facilities (hospitals), ten data structural bodies are written into the card.

Figure 4:
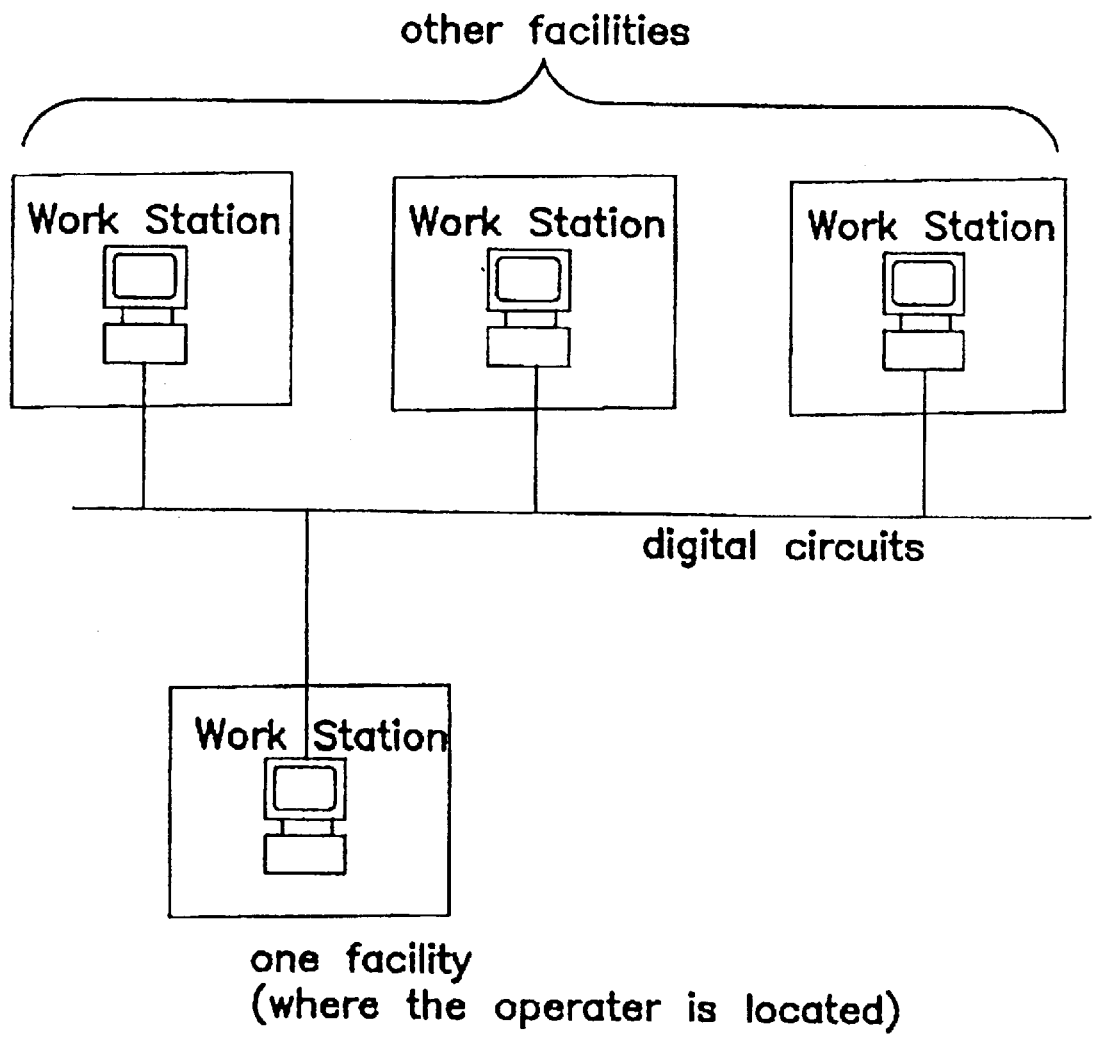
FIG. 4 is an illustration of a system of plural workstations according to the present invention.

As shown in FIG. 4, in the workstation for medical service according to the present invention, when the operator, such as a medical doctor, asks for the retrieval of the data of medical service information in other facilities when diagnosing a patient, the operator effects access to the workstations for medical service in said other facilities by the afore-described data structural bodies through digital circuits.

Such demands for data retrieval of medical service information to other facilities are divided broadly into two kinds. One is header information (information regarding medical service data), and the other is for medical service data themselves. (For example, image data are used therefor.) Generally, medical service data are a great deal of data as compared with header information, and therefore, it is preferable to access to the header information alone at first and retrieve only an identification as to what information is stored in the other facilities, and to access only the necessary medical service data. If the access to the header information is effected when a patient visits the hospital to consult with medical staff, the medical doctor need not effect circuit access while consulting with the patient, and can access to a local memory (a main memory device or disc) in the workstation for medical service, and thus, the consultation time will be shortened. The data of the consultation section and the latest consultation date are effective in the sense of enabling the operator to make a prompt selection of other facilities to be accessed.

Data formats are on the trend toward unification among manufacturers, and in Japan, MIPS (Medical Image Processing System) is the base. The distinction between the aforedescribed header information and medical service data is such that in MIPS, the personal identification code, the patient's name, the names of medical instruments, etc., are the header information, and the waveforms or images collected by means of various medical instruments are the medical service data. However, in MIPS, the header information and the medical service data are preserved and transferred in a continuous memory space, while as regards data formats, it is desirable to manage header information and medical service data as discrete files like ISAC (Image Save And Carry), the standards of which have recently been unified. That is the reason why file length for the header information is altered in a case that both the date and the facility number when any medical service datum is accessed by applying to an operation, are stored into the header information, and further the medical service datum of itself in succession to the header information must also be removed therewith.

The management of the medical service information is basically done in the facilities which have created the information, but in small-to-medium sized facilities, it is difficult to make the medical service information which increases day by day accessible from a circuit for all of an effective period, e.g., three years. In this case, it is necessary to request other facilities or organs to manage the medical service information. When the medical service information transferred to other facilities is accessed to, this workstation needs to have a function for sending back the line number of the transferred facility to the accessed point.

In this manner, the medical doctor becomes able to access all of the medical service information of the patient through the public circuit, but from the viewpoint of a patient, there may be data the patient does not want to disclose even to a doctor. This desire will be accommodated by adding a permission code determined in each datum by the patient, and making the data inaccessible without the patient's consent. The setting of the right to access by the permission code is effected in accordance with the patient's wish in the facilities wherein the medical service information was created, and the setting of the right to access is in each datum. If the number of permission codes for a certain patient in a certain facility is single, the management thereof will be easy.

Another merit of dispersively managing the medical service information using the same data format in the manner described above is the improved accuracy of diagnosis by the retrieval of similar cases. When the doctor retrieves many, and unspecified, data without the aforedescribed card system, a prearrangement between the doctor and the facilities to which an inquiry should be addressed or between the facilities to which the doctor belongs and the facilities to which an inquiry should be addressed, is necessary. When the doctor retrieves many and unspecified data, the setting of the password and permission code becomes invalid. But, when the doctor accesses to many and unspecified data with his or her personal wish, it is necessary to make the reading-out of the patient's name in the header information impossible so that the patient cannot be specified by the operator.

The system hitherto described contributes to clarifying the location of the medical service information on the basis of the card information and to the effective utilization of an individual's medical service information. On the other hand, in a country like Japan in which insurance consultation is advanced, it becomes possible to manage the information of each insurant in the insurance organ to which the payment of a premium should be claimed. The term "information" used here is a list of data structural bodies beginning with the names of facilities utilized by the insurants and facility line numbers. In such a case, the card owned by the patient may have recorded therein a set of insurance data consisting of insurance organ code, insurance organ line number, insurant identification code and insurant password, and a magnetic card of small capacity will suffice as such.

In a system like the present system which utilizes public circuits, the fee for using the circuit (circuit fee) should be borne by the patient and therefore, the function of calculating the total of the fee for using the circuit, and transferring it to a consultation fee calculating computer on the network or displaying it on the CRT of the workstation is necessary.

Figure 1:
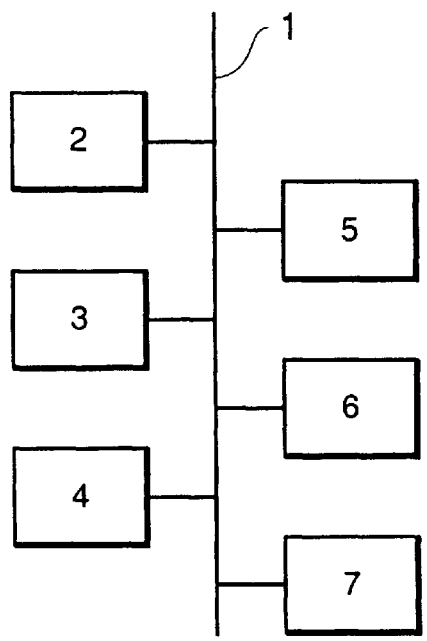
FIG. 1 is a block diagram of a system according to an embodiment of the present invention.

FIG. 1 is a block diagram of the system according to an embodiment of the present invention.

A system bus 1 for connecting modules in the workstation for medical service according to the present invention has connected thereto a CPU 2, a main memory device 3, an input-output apparatus 4 comprising a CRT or a display device such as a liquid crystal display and an operation input device, an ISDN interface 5, a disc 6 and an optical card device 7.

Figure 2:
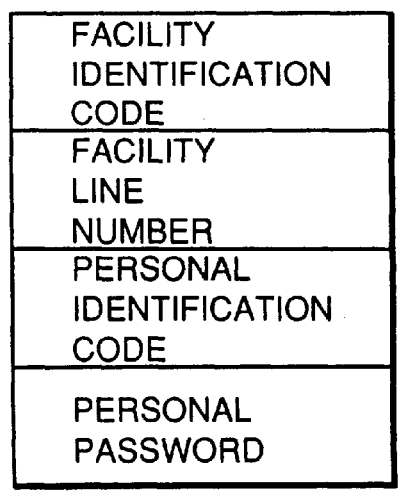
FIG. 2 is an illustration of the data structural body of an optical card.

FIGS. 2 and 3 are illustrations showing the data structural bodies of the optical card. On the data structural bodies of the optical card carried by the patient, in FIG. 2, there are recorded the facility identification code, the facility line number, the personal identification code and the personal password, and in FIG. 3, there are additionally recorded the consultation section code and the latest consultation date.

Figure 5:
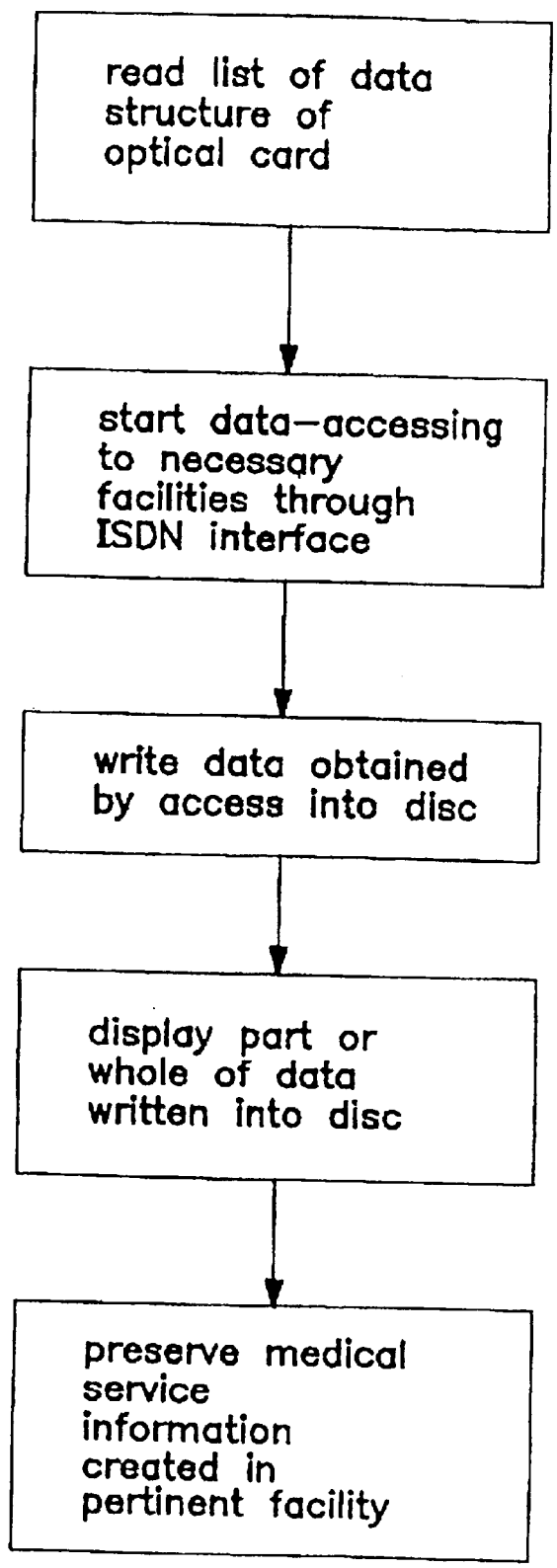
FIG. 5 is a flowchart illustrating overall operation of a system using the present invention.

As outlined in the flowchart of FIG. 5, the optical card carried by the patient is set on the optical card device 7 and the operator commands from the input-output apparatus 4, whereby the list of the data structural bodies of the optical card as shown in FIG. 2 or 3 is read. At that time, data access is effected to the facilities where it is possible that data therein need to be referred or all facilities through the ISDN interface 5.

When the personal identification code in FIGS. 2 and 3 is retrieved as a retrieval key, the personal password in the same data structural body is used to the demand for the personal password, and a permission code memorized by the patient is input from the input-output apparatus 4 to the demand for a permission code. The data obtained by access is written as a temporary file into the disc 6, and part or the whole of the data is displayed on the input-output apparatus 4 in accordance with the operator's instructions. The disc 6 is also utilized for the preservation of medical service information created in the pertinent facilities.

The ISDN interface 5 may be a digital exclusive circuit or a digital public circuit and LAN (local area network) interface. Where the ISDN interface 5 is LAN interface, it is connected to a computer having an external line in the pertinent facilities by LAN.

The disc 6 may preferably be a magnetic disc from the viewpoint of access speed, but may advantageously be an optical disc, a magneto-optical disc or DAT (Digital Audio Tape) in terms of capacity.

The optical card device 7 may be an IC card, a magneto-optical card or a magnetic card.

As described above, the workstation for medical service according to the present invention can achieve the dispersive management and reuse of medical service information among facilities with good timing and effectively. Also, with the higher speed of public and exclusive digital circuits in the future, information reference among facilities can be accomplished easily, and a medical doctor utilizes numerous kinds of data consolidately, whereby the present invention is effective to improve the accuracy of diagnoses of diseases.

What is claimed is:

1. A memory medium for medical service owned by each of plural patients, comprising:

a memory device main body; and a memory portion provided on said main body having stored therein one or more data structures each having at least facility line number data of a respective facility in which medical data of each patient is stored, and said facility line number data being arranged for use in access of the medical data stored in the respective facility through a public or an exclusive line from another facility.

\* \* \* \* \*